United States Patent
Gelbfish

[19]

[11] Patent Number: 6,019,350

[45] Date of Patent: Feb. 1, 2000

[54] HAND HELD CONTROL DEVICE AND ASSOCIATED METHOD

[76] Inventor: Gary A. Gelbfish, 2502 Avenue I, Brooklyn, N.Y. 11210

[21] Appl. No.: 08/811,937

[22] Filed: Mar. 5, 1997

[51] Int. Cl.[7] .................................................. F16K 31/44
[52] U.S. Cl. ...................... 251/321; 200/61.85; 604/249
[58] Field of Search .................................... 251/321, 323, 251/322; 200/61.85, DIG. 2; 604/33, 249

[56] References Cited

U.S. PATENT DOCUMENTS

| | | |
|---|---|---|
| 1,197,652 | 9/1916 | Newton . |
| 1,199,710 | 9/1916 | Newton . |
| 1,230,943 | 6/1917 | Sundh . |
| 1,280,457 | 10/1918 | Harris . |
| 1,527,792 | 2/1925 | French . |
| 1,906,193 | 4/1933 | Vitale . |
| 2,270,363 | 1/1942 | Weeber . |
| 2,812,405 | 11/1957 | Wolkov . |
| 2,878,336 | 3/1959 | Ehrlich . |
| 3,083,278 | 3/1963 | Mukai . |
| 3,142,227 | 7/1964 | Stringer . |
| 3,226,501 | 12/1965 | Seserman . |
| 3,421,160 | 1/1969 | Domenico . |
| 3,532,344 | 10/1970 | Masstab . |
| 3,700,835 | 10/1972 | Rackson . |
| 3,700,836 | 10/1972 | Rackson . |
| 4,696,305 | 9/1987 | von Berg ............................. 604/249 X |
| 4,776,840 | 10/1988 | Freitas et al. . |
| 5,304,763 | 4/1994 | Ellman et al. . |
| 5,388,612 | 2/1995 | Cerola et al. . |
| 5,499,145 | 3/1996 | Wortrich . |
| 5,665,074 | 9/1997 | Kelly ................................... 604/209 X |

*Primary Examiner*—John Fox
*Attorney, Agent, or Firm*—R. Neil Sudol; Henry D. Coleman

[57] ABSTRACT

A manually operated flow control device has a frame with a first part and a second part connected to one another for relative motion alternately towards and away from one another along a line of action. A flow guide is connected to the frame, while a flow modification component is mounted to the frame and is operatively connected to the flow guide for changing a state of flow through the flow guide in accordance with relative positions of the first part and the second part along the line of action. A structure is provided on the frame for enabling a user to hold the frame by exerting a first compressive force on the frame along the line of action between a selected finger of the user, on one side, and a palm surface of the user, on another side, and for further enabling the user to actuate the flow actuation component by exerting a second compressive force on the frame along the line of action between the selected finger and the palm surface, the second compressive force being larger than the first compressive force. The structure for enabling the holding of the frame and the actuation of the flow modification component includes a seat on the frame for receiving or engaging the selected finger so as to resist sliding of the frame off of the selected finger.

5 Claims, 4 Drawing Sheets

HAND HELD CONTROL DEVICE AND ASSOCIATED METHOD

BACKGROUND OF THE INVENTION

This invention relates to a manually operated control device and an associated method. More particularly, this invention relates to a hand-held, finger and palm operated control device and an associated method.

In the medical and dental fields, a health care professional is frequently required to exercise personal control over a number of operating parameters. Although medical and dental instrument are, in many cases, provided with integral finger operated controls, ancillary equipment is frequently used which requires a control separate from the medical or dental instrument. This control has traditionally been provided by means of a foot switch. However, foot switches have very significant limitations. The user is required to stand or sit in an unbalanced position, which is tiring and burdensome. Moreover, the controlling foot tires and may fall and inadvertently actuate the foot switch. Where the user has lost track of the foot switch, he or she must divert their attention away from the patient and the operating instruments to locate the misplaced foot switch. This diversion of attention can lead to inefficiency, loss of concentration and even to accidents, as well. In addition, the cords extending to the foot switch are generally strewn across the floor, provided a hazard to effective negotiation of the floor surface.

A conventional alternative to the foot switch is the assistant. An assistant is disadvantageous for several reasons. The assistant must be told what to do, so there is inevitably a delay between the necessity for action as perceived by the surgeon, doctor or dentist and the completed action as carried out by the assistant. Assistants can fail to properly attend to the ongoing operation and thus be the source of accidents. Assistants take up space in the operating room or dental office. Last but not least, assistants are expensive.

Many proposals have been advanced for attaching switches to the hand. Most such proposals contemplate attaching a switch to the back of the hand. U.S. Pat. No. 3,700,835 to Rackson, however, discloses a hand held, finger controlled switch device which sits on the palm of the user and is connected to a selected nonindex finger of the user via a ring or loop. The switch has upwardly projecting switch levers which are actuated by touch of the finger tips. A wire extends from the switch device and the user's palm in a direction opposite to the base of the thumb. The design enables the user to hold and actuate the switch, while simultaneously permitting the user to use the first two or three fingers. The disadvantages of this configuration, however, soon become apparent. The switch tends to rotate on the user's palm about the selected finger. Because the switch is activated by the finger tips, any rotation is critical. Rotation displaces the switch levers, causing the user to press a wrong button or to divert his attention to looking for the position of the control device and to shifting the device back into place relative to the fingers. This problem is recognized by Rackson, and elaborate means to overcome this limitation are disclosed by him. These means include the above-mentioned ring-like structure common to all the disclosed switched and additional designs with finger enclosures that hold the device in place relative to the finger tips. A further solution to this problem is disclosed in U.S. Pat. No. 3,700,836 to Rackson. In accordance with that solution, the switching device is fastened to the user's palm via a glove, a wrist brace or other kind of bracket.

The control device attached to the hand via a glove or a wrist brace as disclosed in U.S. Pat. No. 3,700,836 is burdensome to a medical or dental practitioner. A glove or a wrist brace restricts the hand and can interfere with conventional medical and dental procedures.

Thus, the prior art discloses a hand-held switch that is activated by several fingers, leaving at least the thumb and the index finger free for use. The prior art fails, however, to propose or suggest a structure for this function that can be comfortably held and actuated in the hand, yet without restrictive and complex wrist, hand and finger attachments. Indeed, the prior art indicates that the effective use of such a switch requires one or more of these cumbersome means so that the switch may be accurately and continuously held in place in the palm of the hand, without inadvertent movement that would preclude its proper function. Considering these insurmountable limitations in the Rackson design and the necessary trade-off that the user must make, there is little wonder why these switches are not in medical or other known use today. This is despite the significant benefits of a switch that permits a single hand to perform dual functions. Certainly, if a simpler and more elegant design solution was thought to exist, it would have been enthusiastically adopted.

OBJECTS OF THE INVENTION

An object of the present invention is to provide a hand held control device which is maintained in the hand and actuated by a simple yet effective method.

A more particular object of the present invention is to provide such a control device which is operated by fingers other than the index finger and the thumb, thereby leaving the index finger and the thumb available for performing other manual tasks.

An additional particular object of the present invention is to provide a control device, held in the hand and operated by fingers other than the index finger and the thumb, yet whose structure and method of use enable continued use despite significant movement within the hand that would normally be expected to occur.

Another object of the present invention is to provide such a control device which has a small number of parts and is accordingly easy and inexpensive to manufacture.

A further object of the present invention is to provide such a control device which can be quickly removed from the hand and easily and quickly reinserted into the hand.

It is a related object of the present invention to provide a method for exercising manual control over a switching function while performing another procedure.

These and other objects of the present invention will be apparent from the drawings and descriptions herein.

SUMMARY OF THE INVENTION

A manually operated flow control device comprises, in accordance with the present invention, a frame including a first part and a second part connected to one another for relative motion alternately towards and away from one another along a line of action. A flow guide is connected to the frame, while a flow modification component is mounted to the frame and is operatively connected to the flow guide for changing a state of flow through the flow guide in accordance with relative positions of the first part and the second part along the line of action. A structure is provided on the frame for enabling a user to hold the frame by exerting a first compressive force on the frame along the line of action between a selected finger of the user, on one side, and a palm surface of the user, on another side, and for further enabling the user to actuate the flow actuation component by exerting a second compressive force on the frame along the line of action between the selected finger and the palm surface, the second compressive force being larger than the first compressive force. The structure for enabling the holding of the frame and the actuation of the flow modification component includes a seat on the frame for receiving or engaging the selected finger so as to resist sliding of the frame off of the selected finger.

In accordance with another feature of the present invention, the flow guide is connected to the one of the parts of the frame and extends substantially parallel to the line of action, whereby the flow guide may extend between the selected finger and an adjacent finger during exertion of the first compressive force and during exertion of the second compressive force. The flow guide thus serves a subsidiary function of helping to maintain the flow control device in the user's hand.

The flow guide may be a wire carrying electrical current or a hydraulic or pneumatic line carrying a fluid. In the former case, the flow modification component is a contact of an electrical switch. In the latter case, the flow modification component is a valve structure.

The flow guide generally includes a first section and a second section each connected to the frame. Preferably, the first section and the second section extend substantially orthogonally relative to one another. Thus, one section of the flow guide can pass between two adjacent fingers of the user's hand while the other section can extend away from the palm in a direction opposite to the thumb of that hand. This orthogonal geometry of the flow guide sections serves to minimize torques tending to rotate the control device from a preferred orientation, the flow guide sections generally exerting balanced opposing torques. In addition, the orthogonal geometry of the flow guide sections serves to have the flow guide bypass the forefinger and thumb area of the hand, leaving that area open for other uses.

Even if the hand-held device slips relative to the hand, the control device can nevertheless be operated properly because the frame has broad contact surfaces (such as the finger seat) designed to engage broad surfaces of the hand, so that force between any two hand parts is sufficient to actuate the device. Thus, the device is functional within a wide range of finger and palm positions and does not need to be held in a fixed predetermined location relative to the hand, thereby eliminating the need for complex connection structures.

Pursuant to a further feature of the invention, the flow guide is operatively connected to a medical device which is held by an index finger and a thumb of a user's hand. The flow control device is operated by another finger and a palm surface of the user's hand.

The finger seat may be a concave or scalloped surface contoured to fit a user's finger.

A method for exercising manual control over a switching function while performing another procedure utilizes a manually operated control device having a biasing spring. The method comprises, in accordance with the present invention, holding the control device between a palm surface of a user's hand and a selected finger of the hand other than an index finger, where the holding of the control device includes pressing the selected finger and the palm surface towards one another to thereby exert a first compressive force on the control device along a line of action extending between the selected finger, on one side, and the palm surface, on another side. The biasing spring exerts a counterbalancing force along the line of action in opposition to the first compressive force. The method further comprises manipulating an instrument with a given index finger and a thumb of the hand while holding the control device between the palm surface and the selected finger by the exertion of the first compressive force. During a continued manipulation of the instrument via the given index finger and the thumb, the control device is deformably compresses along the line of action. The compressing of the control device includes exerting a second compressive force on the control device along the line of action by moving the selected finger and the palm surface towards one another in opposition to a restoring force exerted by the biasing spring, the second compressive force being larger than the first compressive force. By virtue of the deformable compression of the control device along the line of action, a control function is executed during the deformable compression of the control device and only during the deformable compression of the control device.

Where the control device is a flow control device, the execution of the control function includes changing a flow through a flow guide connected to the flow control device. Where the flow guide extends from the flow control device between the selected finger and an adjacent finger of the hand, the method may further comprising gripping the flow guide between the selected finger and the adjacent finger.

In addition, where the flow guide extends from the flow control device between the selected finger and an adjacent finger of the hand, the method optionally includes releasing the flow control device from between the selected finger and the palm surface and thereupon removing the flow control device from the user's hand. After the removing of the flow control device from the user's hand, the flow guide is gripped between the selected finger and the adjacent finger to thereby suspend the flow control device from the user's hand.

Generally, it is contemplated that the holding of the flow control device is implemented primarily by the first compressive force and the second compressive force, in alternation. It is further contemplated that the holding of the flow control device is implemented solely by the first compressive force, the second compressive force and the flow guide, without additional attachment elements.

Thus, a device in accordance with the present invention differs from previously proposed devices in that a valve structure and function is proposed where a compressive force generated by a partially closed hand is used to comfortably hold and keep in place a finger actuated valve. Besides the major components of such a valve, as described above, additional enhancements to holding can be envisioned. These include rough friction surfaces so that the valve does not easily slide from a given position and/or scalloped, rounded or cushioned surfaces so that the valve can easily conform to, and be held by, specific anatomical surfaces or crevices that naturally occur in the partially closed hand.

Where the flow control device is a valve and the flow guide is a tube carrying a fluid, the control function is either (a) arresting flow of the fluid through the tube or (b) permitting flow of the fluid through the tube.

In accordance with a suitable use of the invention, executing the control function includes operatively connecting a suction source to the instrument.

Where the instrument is a medical instrument, the manipulating of the instrument includes performing a medical operation on a patient, the control device being operatively connected to the medical instrument for controlling an operating parameter thereof.

A hand held control device in accordance with the present invention is maintained in the hand by a simple yet effective method. The control device is operated by fingers other than the index finger and the thumb, thereby leaving the index finger and the thumb available for performing other manual tasks, such as operating medical or dental instrumentation. Moreover, the control device can be quickly removed from the hand and easily and quickly reinserted into the hand.

A control device in accordance with the present invention has few parts and is accordingly easy and inexpensive to manufacture.

DESCRIPTION OF THE PREFERRED EMBODIMENTS

Figure 1:
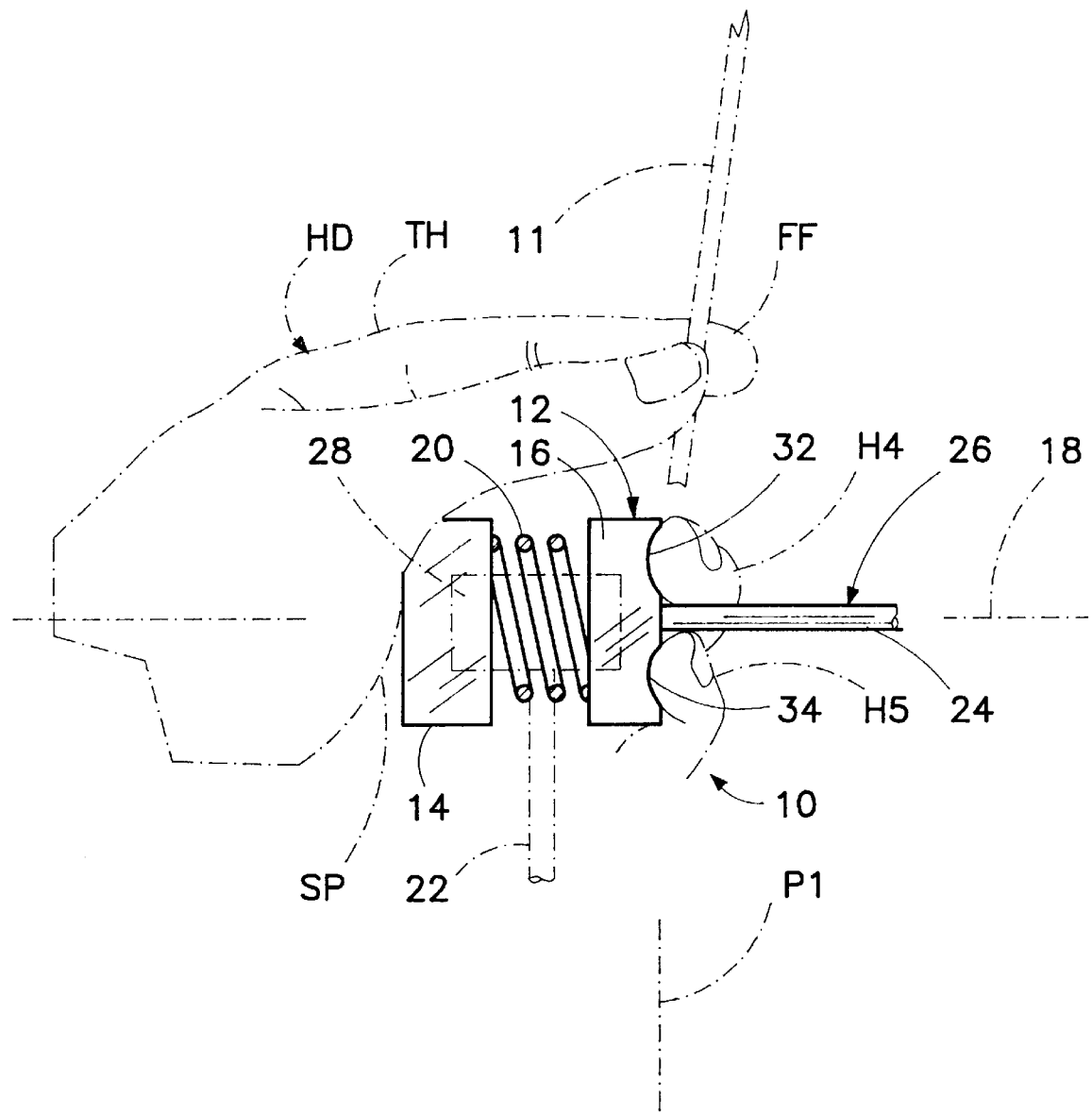
FIG. 1 is a schematic side elevational view, partially in cross-section, of a hand held and hand actuated control device in accordance with the present invention, showing use of the control device pursuant to a method in accordance with the invention.

FIG. 1 devices a hand held and hand actuated control device 10 which is held and operated by pressing the device between the fourth and fifth fingers H4 and H5 of the operator's hand HD, on the one side, and a palm surface SP of the hand HD, on the other side. Generally, a compressive force applied to device 10 via fingers H4, H5 and palm surface SP to hold the device is increased in order to operate the device to control a predetermined function or parameter.

Forefinger FF and thumb TH of hand HD are simultaneously utilized to perform another operation, for example, to manipulate a medical or dental instrument 11. The function controlled by device 10 may pertain to instrument 11, for example to control the energization of instrument 11 or to control an ancillary function such as the application of irrigation or suction via instrument 11. Alternatively, control device 10 may be used to initiate and terminate an operation of another device or instrumentality (not illustrated).

Device 10 includes a frame or housing 12 which is substantially composed of two parts 14 and 16 interconnected for relative motion alternately towards and away from one another along a line of action 18. Frame parts 14 and 16 are connected to one another in part via a compression spring 20. Spring 20 biases frame parts 14 and 16 away from one another along line of action 18.

Frame part 16 is connected to two sections 22 and 24 of a flow guide 26. Flow guide 26 serves for conducting electrical current or a fluid such as air or water. Sections 22 and 24 are oriented perpendicularly to one another, with flow guide section 24 extending parallel to line of action 18 and between fingers H4 and H5. Section 24 serves an ancillary function of limiting lateral displacement of housing 12 relative to hand HD, specifically at fingers H4 and H5. Section 24 may clamped between fingers H4 and H5 by pressing the fingers towards one another.

Device 10 includes a control element such as a valve member or an electrical contract 28 which is disposed in housing 12 for modifying the flow through flow guide 26 in accordance with the relative positions of frame parts 14 and 16 along line of action 18. For example, as frame parts 14 and 16 are moved towards one another in opposition to the biasing or restoring force exerted by spring 20, a predetermined relative position is reached in which valve member or an electrical contract 28 changes the state of flow along guide 26, for example, from a closed or non-existent state of flow to an opened or non-zero flow state.

Housing 12 is provided with a pair of concave finger seats 32 and 34 at one end, for instance, on opposite sides of flow guide section 24. Finger seats 32 and 34 are disposed in a plane P1 oriented extends substantially orthogonally or perpendicularly to line of action 18. Finger seats 32 and 34 receive adjacent fingers H4 and H5 of hand HD and serve to restrict lateral motion or slippage of fingers H4 and H5 relative to device 10. Seats 32 and 34 thus facilitate the holding of housing 12 by exerting a compressive force thereon along line of action 18 between fingers H4, H5 and palm surface SP of hand HD. Spring 20 enables the this holding of housing 12 by exerting a resistive restoring or biasing force which prevents the actuation of valve device 10 unless the compressive force exerted by fingers H4, H5 and palm surface SP exceeds a predetermined threshold magnitude. Accordingly, finger seats 32 and 34 enable an activation of control device 10 and particularly member 28 thereof by exerting an increased compressive force on housing 12 along line of action 18, the increased compressive force being larger than the threshold magnitude.

As discussed below, palm surface PS may be a thenar eminence surface. Other modes of use of device 10 will be apparent from the descriptions presented below with reference to FIGS. 2–4.

Figure 2:
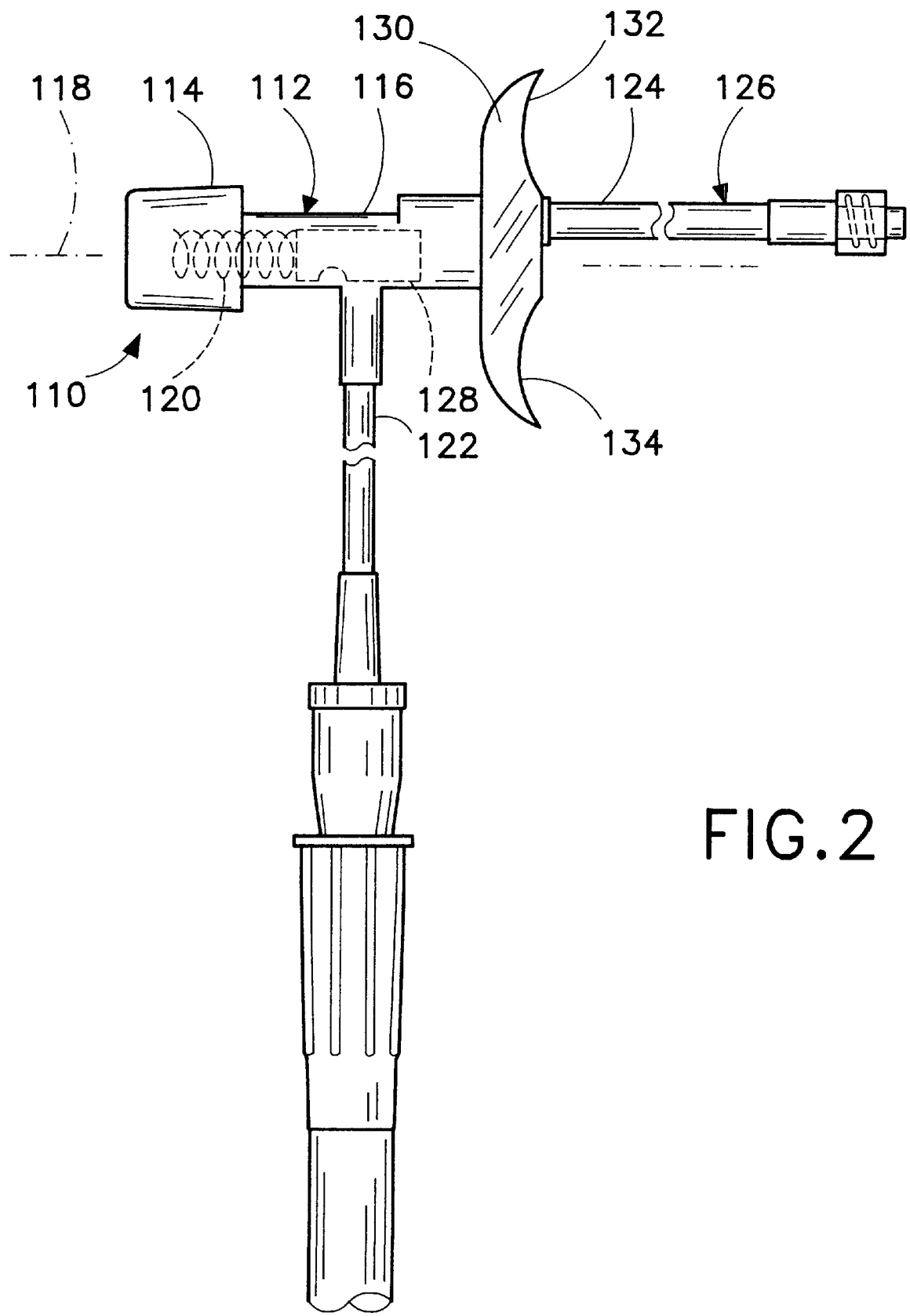
FIG. 2 is a side elevational view of another hand held valve in accordance with the present invention.
Figure 3:
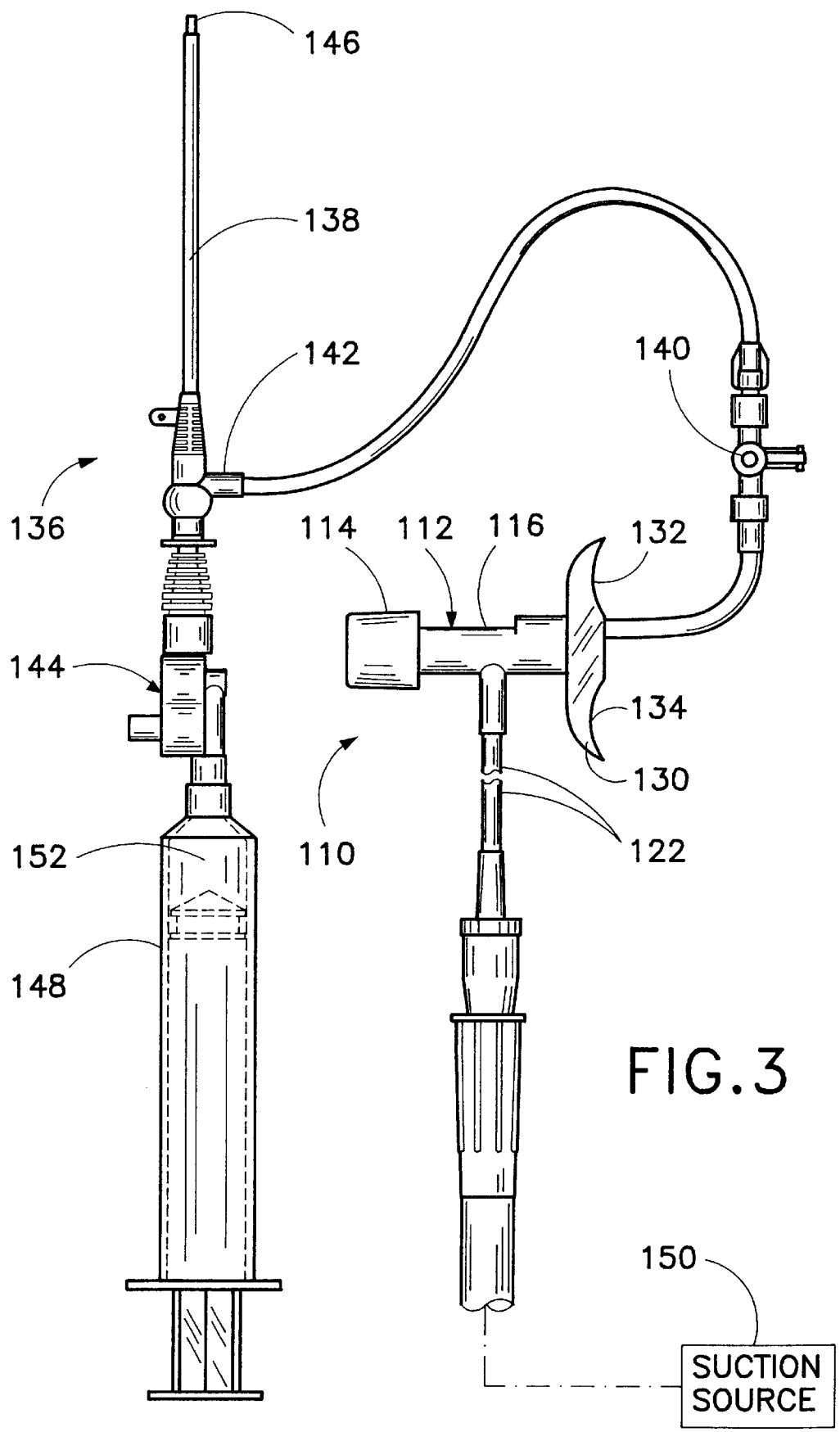
FIG. 3 is a side elevational view of the hand held valve of FIG. 2, showing the valve incorporated into a medical device.
Figure 4:
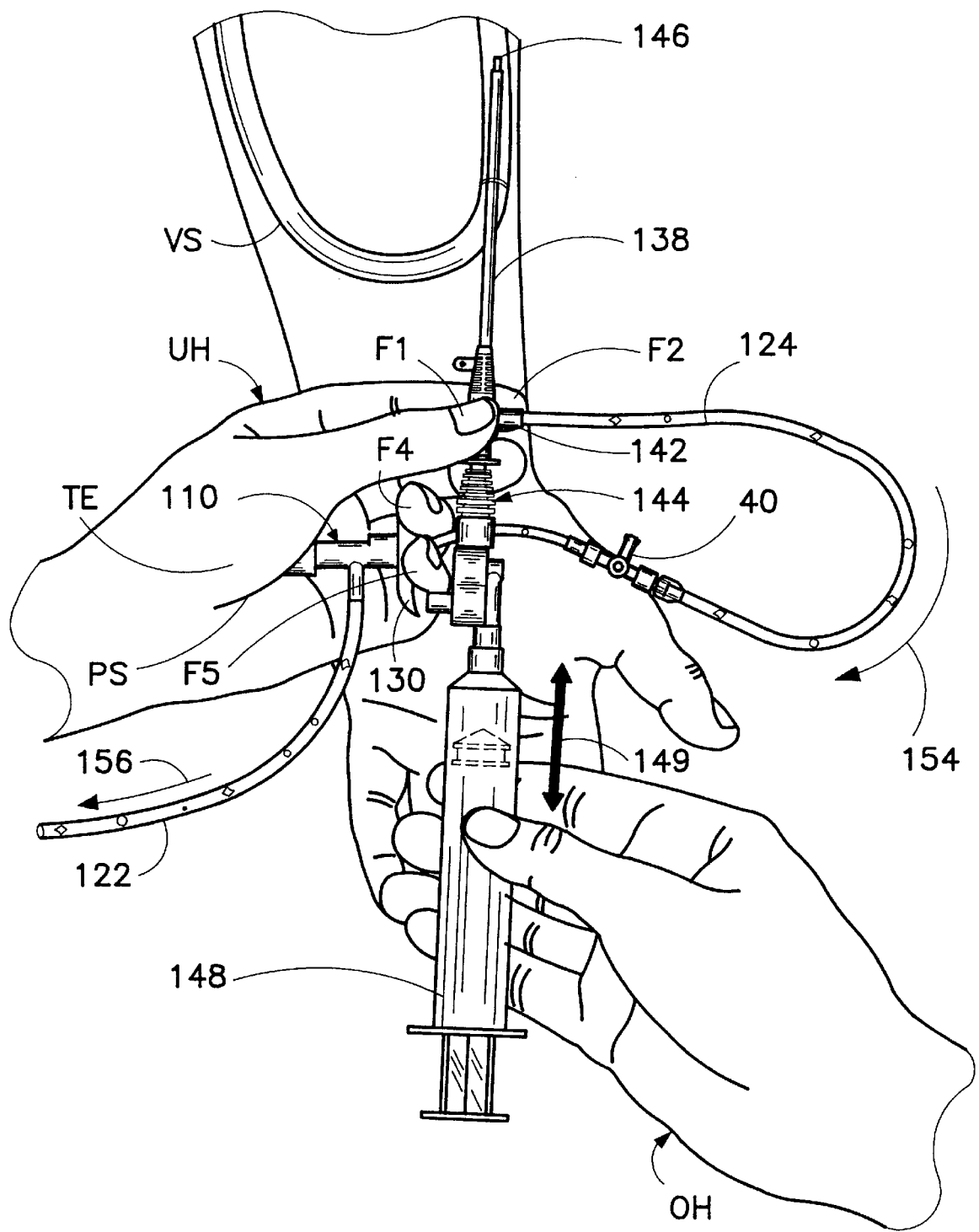
FIG. 4 is a view similar to FIG. 3, depicting use of the medical device and valve of FIGS. 2 and 3.

As illustrated in FIGS. 2 and 3, a hand held valve device 110 includes a frame or housing 112 which is substantially composed of two parts 114 and 116 interconnected for relative motion alternately towards and away from one another along a line of action 118. Housing part 116 is telescopingly received in the manner of a plunger member in one end in housing part 114. Valve housing 112 contains a compression spring 120 which serves to bias housing parts 114 and 116 away from one another along line of action 118.

Housing part 116 is connected to two tube sections 122 and 124 of a flow guide or conduit 126. Flow guide sections 122 and 124 are oriented perpendicularly to one another, with flow guide section 124 extending parallel to line of action 118. A flow-modifying valve member 128, schematically illustrated in FIG. 2, is disposed in housing 112 for alternatively blocking and permitting fluid flow through flow guide 126, depending on the relative positions of housing parts 114 and 116 along line of action 118.

Housing 112 is provided with a finger seat member 130 at one end, particularly the end where flow guide section 124 is connected to housing part 116. Finger seat member 130 extends substantially orthogonally or perpendicularly to line of action 118 and flow guide section 124 and is provided with a pair of concave surfaces 132 and 134 for receiving adjacent fingers F4 and F5 of a user's hand UH, as shown in FIG. 3. Finger seat member 130 enables a user to hold housing 112 by exerting a compressive force thereon along line of action 118 between fingers F4 and F5, on one side, and a palm surface PS of hand UH, on another side. Spring 120 assists in the holding of housing 112 between fingers F4, F5 and palm surface PS by exerting a resistive restoring or biasing force which prevents the actuation of valve device 110 unless the compressive force exerted by fingers F4, F5 and palm surface PS exceeds a predetermined threshold magnitude. Accordingly, finger seat member 130 further enables the user to actuate valve device 110 and particularly flow actuation component or valve member 128 thereof by exerting an increased compressive force on housing 112 along line of action 118, the increased compressive force being larger than the threshold magnitude. Finger seat member 130 and specifically surfaces 132 and 134 thereof receive or engage fingers F4 and F5 so as to resist sliding offrame or housing 112 off offingers F4 and F5.

Valve device 110 is especially effective when palm surface PS is a surface of the thenar eminence TE of hand UH. In that mode of use, it is easy to compress housing 112, i.e., to move parts 114 and 116 towards one another in opposition to the biasing or restoring force exerted by spring 120. It is to be noted that the thenar eminence is anatomically the proximal phalanx portion of the thumb finger and not technically part of the palm. In common, nonmedical usage, however, the thenar eminence is considered to be part of the palm surface and is to be considered as such for purposes of the present disclosure.

Valve device 110 is designed for holding and actuation by the end fingers F4 and F5 (FIG. 3), whereby the index finger F2 of the same hand UR may be used with the thumb F1 thereof for manipulating a medical instrument 136. As shown in FIGS. 2 and 3, flow guide or tube section 124 is connected to a vascular introducer sheath 138 via a stop cock or valve 140 and a port 142. The distal end of sheath 138 is inserted into a vascular shunt or blood vessel VS. Slidably inserted in introducer sheath 138 is a thrombectomy device 144 which has a cutting head 146 at a distal end and a syringe 148 at a proximal end. As shown in FIG. 3, the user holds introducer sheath 138 with index finger F2 and thumb F1 of hand UH. As discussed above, valve device 110 is held in the user's hand UH between thenar eminence TE and fingers F4 and F5. The user's other hand OH grasps thrombectomy device 144 and particularly syringe 148 thereof Hand OH moves alternately towards and away from hand UH (double headed arrow 149), thereby reciprocating thrombectomy device 144 and particularly cutting head 146 in introducer sheath 138. To remove severed organic material (e.g., thrombus or clot) from introducer sheath 138, the user compresses valve housing 112 between fingers F4, F5 and palm surface PS, thereby shifting valve member 128 to open communication between flow guide sections 122 and 124. Flow guide section 122 is connected to a vacuum or suction source 150 for drawing severed organic material from sheath 138 through flow guide 126, as indicated by arrows 154 and 156. Syringe 148 is actuated by hand OH for injecting an irrigation solution 152 into introducer sheath 138.

It is to be noted that flow guide section 124 extends between fingers F4 and F5 during use of the valve device 110, as shown in FIG. 3, and particularly during the application of compressive force to housing 112 to hold and/or to compressingly actuate the housing. Flow guide section 124 thus serves a subsidiary function of helping to maintain device 110 in user's hand UH. Concave surfaces 132 and 134 of finger seat member 130 and flow guide section 124 both resist lateral slippage of valve housing 112 relative to fingers F4 and F5.

Flow guide section 124 serves yet another function. Should the user (surgeon, radiologist, dentist, etc.) require full use of hand UH, valve device 10 may be temporarily dropped from hand UH with flow guide or tube section 124 still extending between fingers F4 and F5 to suspend the valve device 110 from fingers F4 and/or F5. Fingers F4 and F5 can grip the tube section 124, if necessary. Thus, after the use of the entire hand, the valve device 110 may be quickly retrieved and reinserted between fingers F4 and F5, on the one side, and palm surface PS, on the other side.

Valve device 110 is particularly efficacious in controlling a function pertaining to medical instrument 136. Here, valve device 110 is directly connected to instrument 136 via flow guide section 124. The health care professional maintains valve device 110 under his or her direct control and in close proximity to the site of the medical operation. This proximity facilitates the execution of the operation. Also, the lengths of tubes may be reduced, eliminating or decreasing operating room clutter.

As shown in FIG. 3, section 124 of flow guide 126 passes between adjacent fingers F4 and F5 while section 122 extends away from the palm of user's hand UH in a direction opposite to the thumb F I of that hand. This orthogonal geometry of flow guide sections 122 and 124 serves to minimize torques tending to rotate valve device 10 from a preferred orientation between fingers F4, F5 and palm surface PS, the flow guide sections 122 and 124 generally exerting balanced opposing torques. In addition, the orthogonal geometry of flow guide sections 122 and 124 serves to have the flow guide bypass the forefinger and thumb area of hand UH, leaving that area open for other uses.

Generally, it is contemplated that the holding of valve control device 110 is implemented primarily by the compressive force applied via fingers F4, F5 on the one side and palm surface PS on the other side. The compressive force alternates between (1) a decreased value less than the predetermined magnitude or threshold value required to cause valve actuation and (2) an increased value greater than the predetermined magnitude. Generally, spring 120 has a spring constant which is sufficiently great to prevent actuation of valve member 128 while enabling housing 1I12 to be held by the decreased compressive force. In addition, the spring constant of spring 120 is sufficiently small to enable actuation of valve member 128 by the increased compressive force.

Valve device 110 is easy to manufacture. Spring loaded valves similar to housing 112 exist and are used in many industrial and consumer items including in musical trumpets and in medical applications. These valves are commonly available and sourced by original equipment manufacturers (OEMs). The valves are designed for, and have always been activated via, pressing the plunger via a finger tip while the lower body member (part 1I14) of the valve is held in a stable, and otherwise independently secured, enclosure or device. A simple inspection of such a valve when it is independent of its necessary holding enclosure will show that indeed it cannot be comfortably held in the hand or used in any way similar to what is described herein. In order to permit such an unanticipated use, with its attendant unexpected results, the valve requires the addition of finger seat 130. Finger seat member 130 may be injection molded and secured in a press-lock fit to housing part 116 or may be integrally molded onto the valve body. Thus, the addition of this finger seat transforms an otherwise common spring loaded valve mechanism into a different structure that is non-obvious and that becomes useful in the novel and highly significant ways that are discussed above.

Although the invention has been described in terms of particular embodiments and applications, one of ordinary skill in the art, in light of this teaching, can generate additional embodiments and modifications without departing from the spirit of or exceeding the scope of the claimed invention. For example, the structural and operating principles of valve device 110 apply where the device is an electrical switch rather than a pneumatic or hydraulic switch (valve). In that case, valve member 128 is an electrical switch contact while flow guide sections 122 and 124 are wires or cables.

Instead of a single spring, a control device may incorporate a plurality of springs, for example, a first spring for exerting a counterbalancing force to facilitate holding of the control device and a second spring with a higher spring constant for preventing actuation of the control device unless the applied compressive force exceeds a threshold value determined by the higher spring constant. For purposes of the instant disclosure, the two springs function in an equivalent manner to a single spring.

In addition, the function of a compression spring may be performed by other, equivalent, force exerting elements, such as magnets with repelling poles or pneumatic or hydraulic pressure chambers.

Accordingly, it is to be understood that the drawings and descriptions herein are proffered by way of example to facilitate comprehension of the invention and should not be construed to limit the scope thereof.

What is claimed is:

1. A manually operated control device comprising:

a frame including a first part and a second part movably connected to one another;

a control component mounted to said frame for changing a control parameter in accordance with relative positions of said first part and said second part;

a spring mounted to said frame for biasing said first part and said second part away from one another along a line of action, said spring having a spring constant sufficiently great to prevent actuation of said control component while enabling said frame to be held by a first compressive force exerted on said first part and said second part tending to move said first part and said second part towards one another, said spring constant being sufficiently small to enable actuation of said control component by a second compressive force exerted on said first part and said second part tending to move said first part and said second part towards one another, said second compressive force being greater than said first compressive force;

a finger engagement surface on one of said first part and said second part enabling a manual application of said first and said second compressive force, said finger engagement surface extending substantially perpendicularly to said line of action, said finger engagement surface being formed to resist sliding of said frame off of a selected finger; and a flow guide connected to said one of said first part and said second part and extending substantially parallel to said line of action, whereby said flow guide may extend between adjacent fingers of a user during a holding of said frame between said selected finger on one side, and a thenar eminence of the user, on another side, said control component being operatively connected to said flow guide for changing a flow through said flow guide in accordance with relative positions of said first part and said second part, said control parameter being the flow through said flow guide.

2. The device defined in claim 1 wherein said flow guide includes a first section and a second section each connected to said frame, said first section and said second section extending substantially orthogonally relative to one another.

3. The device defined in claim 1 wherein said flow guide is a hydraulic or pneumatic line.

4. The device defined in claim 1 wherein said flow guide is operatively connected to a medical device which is held by an index finger and a thumb of a user's hand, while the flow control device is operated by said selected finger and a palm surface of the user's hand.

5. The device defined in claim 1 wherein said finger engagement surface is formed with a concavity to resist sliding of said frame off of a selected finger.

* * * * *